United States Patent [19]

Argyropoulos et al.

[11] Patent Number: 4,883,906

[45] Date of Patent: Nov. 28, 1989

[54] PRODUCTION OF TRISUBSTITUTED HYDROXYALKYL ALKANOATES FROM ALDEHYDES

[75] Inventors: John N. Argyropoulos, Dunbar; Edmond J. Derderian; Brian T. Keen, both of Charleston; Timothy G. Bumgardner, Liberty, all of W. Va.

[73] Assignee: Union Carbide Corporation, Danbury, Conn.

[21] Appl. No.: 125,139

[22] Filed: Nov. 25, 1987

[51] Int. Cl.$^4$ .............................................. C07C 69/28
[52] U.S. Cl. .................................... 560/238; 560/248; 560/252
[58] Field of Search ..................... 560/238, 248, 252

[56] References Cited

FOREIGN PATENT DOCUMENTS 3447029  6/1986  Fed. Rep. of Germany ...... 560/238

*Primary Examiner*—Bruce Gray
*Attorney, Agent, or Firm*—Morris N. Reinisch

[57] ABSTRACT

A process for producing and refining trisubstituted glycol monoesters, e.g., 2,2,4-trimethyl-1,3-pentanediol monoester. The improvement resides in immediately distilling the crude condensation product mixture as it leaves the reactor before it has cooled or had any contact with added water.

26 Claims, 2 Drawing Sheets

PRODUCTION OF TRISUBSTITUTED HYDROXYALKYL ALKANOATES FROM ALDEHYDES

FIELD OF THE INVENTION

This invention relates to an improved process for producing trisubstituted glycol monoesters particularly the trisubstituted hydroxyalkyl alkanoates. More specifically it pertains to a process for minimizing formation of undesirable by-products that present problems in recovery of the trisubstituted glycol monoesters and reduce the yields.

DESCRIPTION OF THE PRIOR ART

The production of trisubstituted hydroxyalkyl alkanoates, e.g., the isomers of 2,2,4-trimethyl-1,3-pentanediol monoisobutyrate (2,2,4 trimethyl-3-hydroxypentyl isobutyrate and 2,2,4-trimethyl-1-hydroxypentyl isobutyrate), has been described in U.S. Pat. No. 3,091,632, issued to H. J. Hagemeyer et al. on May 28, 1963. This patent describes a process for producing the glycol monoesters by the reaction of an aldehyde in contact with a metal alkoxide catalyst under essentially dry, acid free conditions. The reaction is conducted at about 65° C. to 105° C. at a catalyst concentration less than two weight percent based on the aldehyde and a residence time of less than three hours; the catalyst is added as an alcohol solution. At the conclusion of the condensation reaction, the condensation product was conveyed to a mix tank where water was added and then to a stripping column to azeotropically recover unreacted aldehyde and to reverse any aldol formed in the process. The first step in product recovery was this water treatment; refining followed by drying and distilling the water treated reaction product mixture after the unreacted aldehyde had been azeotropically removed by the water treatment.

In U.S. Pat. No. 3,291,821, issued to M. A. Perry et al. on Dec. 13, 1966, there is described a process for preparing glycol monoesters by condensation of aldehydes using an aqueous solution of a strong inorganic base as the catalyst. A long, complicated recovery system is used to recover the product necessitating the use of two decanters (12 and 21) and four distillation columns (17, 24, 27 and 30), as is shown in the drawing and summarized in column 2, lines 15 to 38 of U.S. Pat. No. 3,291,821. The recovery process disclosed in this patent conducts the crude reaction mixture from the reactor 1 to first decanter 12 to initially separate the aqueous phase from the desired organic phase. The recovered organic phase is introduced into the first stripping column 17 and water is added in the first step of the refining process; after azeotropically distilling to strip off the aldehyde and aldols the bottoms are introduced into a second decanter 21 to recover the organic phase. The organic phase is dried in a second distilling column 24 to remove water overhead; the dried bottoms are introduced into a third distilling column 27 and glycols are stripped overhead. The bottoms are then introduced into a fourth distilling column 30 with the refined glycol monoester recovered overhead and the bottom residues discarded. The recovery and purification process requires two decantation steps and four distillations. The process described in U.S. Pat. No. 3,291,821 requires an initial treatment of the crude reaction product with water in first column 17 in order to remove the unreacted aldehyde. It was only after the reaction product had been treated with water was an attempt made to remove the aldehyde in column 17 and these steps were then followed by another decantation (21) and three distillations 24, 27, 30. In addition, as shown in the specification and claims, a large quantity of water is present in the reactor, the volumetric aldehyde to aqueous catalyst solution being from about 90:10 to about 50:50.

In U.S. Pat. No. 3,718,689, issued to J. H. McCain et al. on Feb. 27, 1973, a process for preparing the trisubstituted hydroxyalkyl alkanoates was described that involved use of the catalyst as a concentrated aqueous solution of the base, its concentration being from about 30 to about 60 weight percent. Further, the amount of aqueous base solution used was such that the reaction mixture was essentially homogeneous and separation into two layers or phases does not occur on standing for several hours (column 3, lines 23 to 60); whereas, in U.S. Pat. No. 3,291,821 separation in about 30 minutes was preferred (column 3, lines 50 to 57). The recovery process described in U.S. Pat. No. 3,718,689 conducts the reaction product through a total of two decantation steps, one in-line mixing step and five distillation steps. The initial crude reaction product is introduced into a first distillation stripping column 17 where it is steam stripped to remove unreacted isobutyraldehyde overhead and organic salts in aqueous solution as a bottoms fraction. The product from this column goes through a double decantation with an intermediate water wash through decanters 28 and 33 and in-line mixer 32. After these aqueous treatment procedures the recovered organic phase is dried in distillation column 37, the dry partially refined crude is flash distilled in flash evaporator 41 and then passed through two distillation columns 44 and 48 before recovering the desired refined product; a time consuming, expensive operation that requires considerable capital investment and in which the reaction product mixture is contacted with an aqueous medium as the first step in the refining process.

It is important to note that in the prior art processes the first step in refining the reaction product mixture removed from the reactor was to contact it with an aqueous medium, steam or water.

SUMMARY OF THE INVENTION

An improved process for producing and refining trisubstituted glycol monoesters such as the trisubstituted hydroxyalkyl alkanoates. In this process the crude condensation reaction product mixture produced is subjected to distillation after it leaves the reactor and before it has cooled or had any contact with added water.

DESCRIPTION OF THE INVENTION

The production of trisubstituted hydroxyalkyl alkanoates, hereafter called trisubstituted glycol monoesters, of the structural formula:

wherein X is a hydrogen atom or a group with the proviso that at any one time only one X group is a hydrogen atom and R and R" are as hereinafter defined such as 2,2,4-trimethyl-3-hydroxypentyl isobutyrate and 2,2,4-trimethyl-1-hydroxypentyl isobutyrate, by the catalytic condensation of aldehydes, such as isobutyraldehyde, using a strong base catalyst is well known and has been practiced commercially for decades. A problem associated with this reaction is the unwanted formation of by-products, e.g., dimers, trimers, diols, esters, diesters and organic salts, that are difficult to remove and severely complicate the recovery of the desired product. In the past this recovery has also been further complicated by additional by-products formation that occurs during the purification steps, and has required multiple decantations and distillations before one obtained a commercially acceptable product, as shown by the prior art discussed. This necessitated a significant capital investment for the equipment and significant operating expenses.

It has now been found that the amount of by-products formed can be significantly reduced and, further, that the -purification process can be significantly simplified. In the process of this invention the purification problems associated with the previously disclosed processes can, unexpectedly, be significantly alleviated by an initial distillation of the reaction product immediately after it leaves the reactor and before it has cooled or come into contact with added water in any form; in addition it has been found that subsequent washing of the distilled product obtained from this initial distillation to remove basic metal cations followed by separation of the layers, e.g., centrifugation or decantation, and distillation of the washed organic phase produces a product of exceptionally high purity and a minimum of by-products. By the term "added water" is meant water, steam, or any aqueous containing mixture that is intentionally added to the mixture after the condensation reaction and does not include any water initially present in the reactants or catalyst composition. The process of this invention accomplishes all of this in a significantly fewer number of operations than were heretofore considered necessary.

It was also found that the stability of desired trisubstituted glycol monoesters of Formula I is significantly affected by the temperature and residence time of the reaction product in the first distillation column. It was unexpectedly discovered that as these conditions increased there was an increase in decomposition of the trisubstituted glycol monoesters of Formula I to diol and diester. It was an unexpected rapid decomposition at residence times and temperatures exceeding about 0.5 hour and 200° C., respectively, and may be attributable to the fact that the product is still in contact with the alkali metal catalyst.

In view of the potential harmful effect of the continued presence of metal salts in the reaction product its removal by water-washing was found of significant benefit after the reaction product had undergone the initial, immediate distillation. At least one, and preferably more than one, water washings are of significant benefit in obtaining refined product having a purity of up to about 98 percent or higher, as will be shown infra. However, even in the absence of the water-wash the amount of undesirable products is significantly reduced. The water wash minimized the decomposition of the trisubstituted glycol monoester of Formula I in subsequent refining of the concentrate to recover the purified trisubstituted glycol monoester.

In the practice of the invention, aldehydes are condensed in a continuous flow tubular reactor using an aqueous solution of a strong base, e.g., alkali metal hydroxides or alkaline earth metal hydroxides, the concentration of the strong base in the aqueous solution preferably being at least 30 weight percent; or an alkali metal alkoxide. The condensation process is fully described in U.S. Pat. No. 3,718,689 and being carried out at from about 50° C. to about 150° C.

The reaction can be represented by the following equation:

wherein R' and R", individually represent the same or different monovalent hydrocarbyl radicals, e.g., alkyl, cycloalkyl, aryl, etc., wherein the number of carbon atoms in R' and R" can be from 1 to about 10, preferably 1 to about 4. Illustrative of such radicals are methyl, ethyl, n-propyl, isopropyl, n-butyl, n-hexyl, 2-ethylhexyl, cyclohexyl, cyclopentyl, phenyl, benzyl, tolyl, phenethyl, and the like. Preferably, R' and R" represent the lower alkyl radicals having from 1 to about 4 carbon atoms.

The aldehydes suitable as reactants are $C_4$–$C_{12}$ aldehydes which contain one hydrogen atom on the carbon atom which is positioned alpha to the aldehydic group. Illustrative thereof one can mention isobutyraldehyde, alpha-methylvaleraldehyde, alpha-methylcaproaldehyde, alpha ethylbutyraldehyde, alpha ethylcaroaldehyde, 2-methylheptanal, 2-ethyloctanol, alpha-phenylpropionaldehyde, alpha cyclohexylpropionaldehyde, alpha-phenylbutyraldehyde, and the like. The preferred aldehyde is isobutyraldehyde. Trace amounts of water and organic acid impurities can be tolerated, as known.

The strong bases which are suitable include sodium hydroxide, potassium hydroxide, lithium hydroxide, magnesium hydroxide, sodium methoxide, potassium ethoxide, lithium ethoxide, and the like, with sodium hydroxide the preferred.

The concentration of alkali metal hydroxide in the aqueous catalyst solution is at least 30 weight percent, preferably at least about 35 weight percent, and should not exceed an amount where the resulting aqueous solution ceases to be a liquid at ambient room temperature of about 22° C. An aqueous solution of metal hydroxide in which the concentration of metal hydroxide is about 60 weight percent represents a preferred upper limit. The concentration of alkali metal hydroxide catalyst present in the reactor can be from about 0.1 to 2 mole percent, preferably from 0.3 to 0.8 mole percent, based on the aldehyde. The alkali metal alkoxides are used in anhydrous media.

The condensation reaction is conducted for a period of time at least sufficient to produce a reaction product mixture rich in trisubstituted glycol monoester product of Formula I. In general, a residence period in the reactor of less than about two hours gives satisfactory results. However, marked increases in productivity are obtained by maintaining a residence period of at least about 3 minutes, preferably at least about 6 minutes. Moreover, such productivities are realized without sacrificing either conversion or efficiency at such short periods.

The condensation reaction is effected at an elevated temperature. A suitable temperature range is from about 50° C. to about 150° C. In the practice of preferred embodiments a temperature of from about 70° C. to about 130° C. is employed. Pressures are not critical and satisfactory results are obtained by using atmospheric pressure or moderately superatmospheric pressure, e.g., about one to 10 atmospheres, to minimize vaporization in the reactor.

The reaction product mixture or effluent from the longitudinal flow tubular reactor contains the desired trisubstituted glycol monoester of Formula I, hydroxyalkyl alkanoate, unreacted aldehyde, water introduced with the alkali metal hydroxide catalyst solution and by-products and catalyst residues. Among the by products are small amounts of dimer and trimer, monoesters, diesters, diol, alcohols and organic acid salts.

The effluent may then be preheated before it is directly introduced into a distillation column. Unreacted aldehyde is recovered as a dry side stream and recycled, water added with the catalyst solution is removed overhead and crude concentrated reaction product is removed as a bottoms stream and transferred to a vessel for storage prior to further purification. This first direct distillation is an important and critical feature of this invention and must be carried out before the reactor effluent cools or comes into contact with added water. The average residence time of the effluent in this distillation column can vary from about 5 to about 240 minutes, preferably from about 10 to about 60 minutes; the distillation can be carried out at from about 200 torr to about 1,000 torr, preferably in an inert atmosphere.

The residence time and temperature of the crude concentrated reaction product in the kettle of this first distillation column is also important. The presence of the crude concentrate in the kettle for too long a period at too high a kettle temperature is detrimental and results in decomposition of desired trisubstituted glycol monoester of Formula I to unwanted diol and diester that complicate subsequent purification. The kettle temperature can vary from about 150° C. to about 210° C., preferably from about 160° C. to about 200° C. and most preferably from about 180° C. to about 190° C. The residence time should not exceed about 120 minutes, preferably less than about 60 minutes, and most preferably less than about 30 minutes. The lower the temperature in the kettle, the longer is the residence time that can be tolerated. After the effluent from the reactor has undergone this initial distillation it can be stored at ambient conditions until further purification is desired.

The crude concentrate is further purified by water washing and a second distillation. The crude concentrate recovered from the first distillation column is subjected to one or more water-washes, preferably at least two, before the second distillation. The amount of water used in each wash can vary to a considerable extent and can be as high as 20 volume percent or more based on the crude concentrate. Preferably the first wash uses a concentration of about 10 volume percent and the subsequent washes use less, say up to about 5 volume percent. It was observed that two washes, the first using about 10 volume percent and the second using about 4 volume percent were more effective than a single wash that used about 20 volume percent water. After each wash the phases are allowed to separate with the lower aqueous phase removed as a bottom stream and discarded and the upper organic phase recovered for purification. In the wash inorganic metal salts and organic acid salts containing the catalyst cation are removed. The washed crude concentrate is then introduced into a second distillation column and the desired trisubstituted glycol monoester of Formula I is recovered via conventional fractional distillation.

The process can be more fully understood by reference to the drawings.

Figure 1:
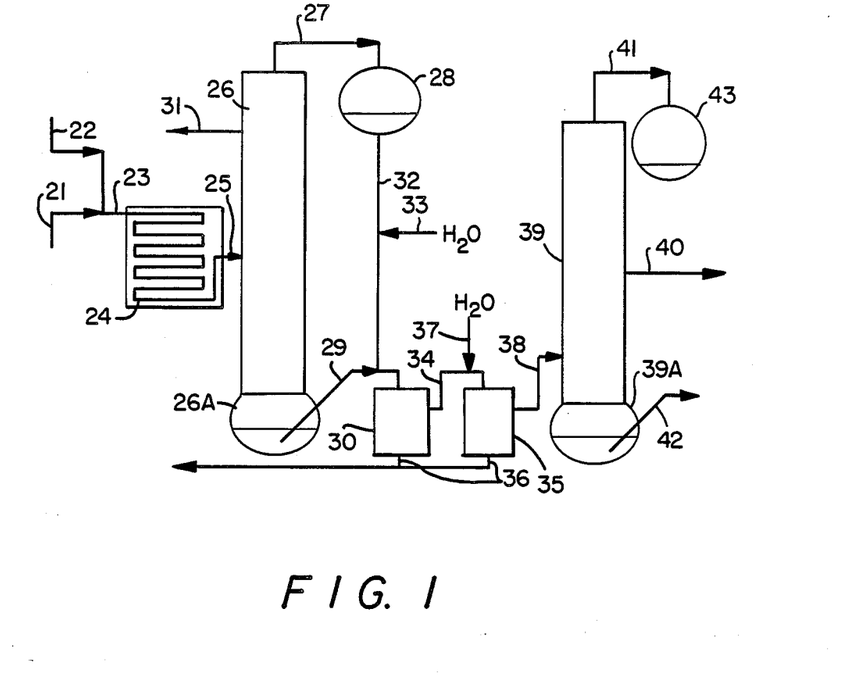
FIG. 1 is a schematic flow diagram of a system for carrying out the invention and FIG. 2 is a graphic representation illustrating the effect kettle residence time and temperature have on the stability of the isomeric mixture 2,2,4-trimethyl-1,3-pentanediol isobutyrate.

Referring to FIG. 1, the aldehyde is continuously fed into line 21 and joined by concentrated catalyst solution, continuously introduced via line 22, the feed rates of each maintained to obtain the desired catalyst concentration in the feed. The resulting mixture flows through line 23 into tubular reactor 24, which can be insulated, maintained at an elevated temperature and pressure. The effluent from tubular reactor 24 is conveyed via insulated line 25 into the mid-section of a multi-tray distillation column 26. Insulated line 25 can be equipped with heating means. Dry aldehyde is recovered as a side stream via line 31 and recycled into the system via line 21. Water and a small amount of unreacted aldehyde are removed overhead via line 27, and conveyed to vessel 28, crude concentrated reaction product is removed from kettle 26A at base of column 26 via line 29 and conveyed to a storage vessel, not shown, from which it is conveyed to wash vessel 30. The aqueous composition in vessel 28 is separated, with the aldehyde being recycled to distillation column 26 and the water conveyed via line 32 into wash vessel 30, additional water being introduced to line 33 or vessel 30 via line 33. The washed reaction product is withdrawn from wash vessel 30 and conveyed via line 34 into wash vessel 35 with the wash water being withdrawn via line 36 and discarded. Water is introduced into wash vessel 35 via line 37 for the second water wash. The washed reaction product is withdrawn from wash vessel 35 via line 38, which can be equipped with heating means, and conveyed into multi-tray distillation column 39; the wash water is withdrawn via line 36 and discarded. Refined product is recovered from column 39 via line 40, lights and trace amounts of water are removed overhead via line 41 into receiver 43 and residue from bottom kettle 39A is removed via line 42.

Figure 2:
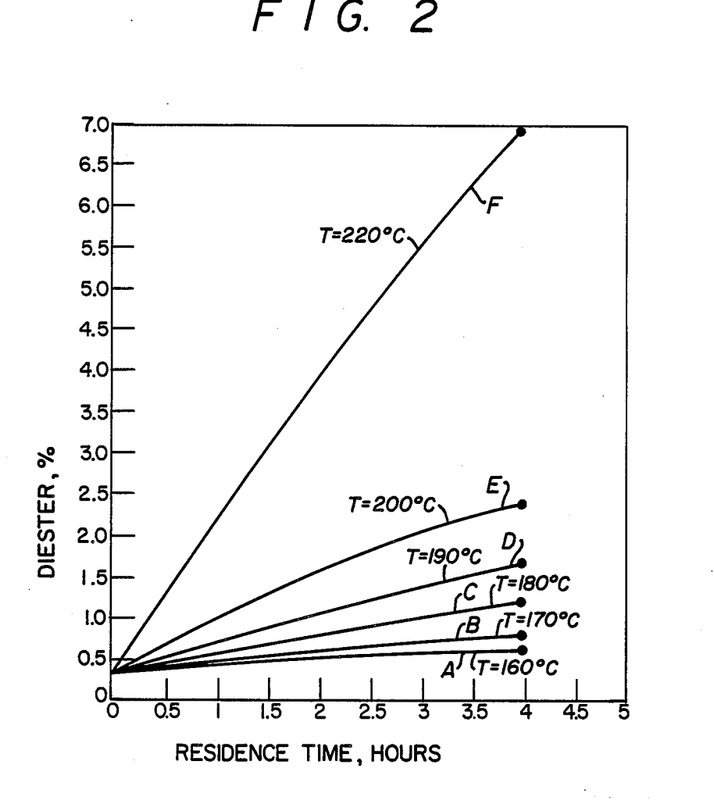

Referring to FIG. 2, this drawing graphically illustrates the unexpected and unpredictable effect residence time and temperature have on the stability of the 2,2,4-trimethyl-1,3-pentanediol isobutyrates during the first distillation. The data in this figure derives from Example 2.

Curve A, based on Series A of Example 2, simulates an initial distillation wherein the temperature of the contents at the base of distillation column 26 would be maintained at 160° C.±3° C. over a four hour residence period. Samples were removed after the material had been subjected to this temperature for average residence times of 0.25 hour, 1 hour, 2 hours and 4 hours. As shown by Curve A, the amount of diester in the sample showed a gradual slight increase with time from an initial diester content of about 0.35 weight percent to about 0.65 weight percent.

Curve B, based on Series B of Example 2, shows similar data obtained when the temperature would be maintained at 170° C.±3° C.

Curve C, based on Series C of Example 2, shows similar data obtained when the temperature would be maintained at 180° C.±3° C.

Curve D, based on Series D of Example 2, shows similar data obtained when the temperature would be maintained at 190° C.±3° C.

Curve E, based on Series E of Example 2, shows similar data obtained when the temperature would be maintained at 200° C.±3° C.

Curve F, based on Series F of Example 2, shows similar data obtained when the temperature would be maintained at 220° C.±3° C.

As shown in the curves for Series A to E, temperatures of from 160° C.±3° C. to 200° C.±3° C. show minimal increases in diester formation at 0.5 hour residence time; even at 1 hour residence time increase in diester formation is not significant. However, as seen in the curve for Series F, at a temperature of 220° C.±3° C., there is an immediate and dramatic increase in diester formation even at 0.5 hour residence time.

The following examples serve to further illustrate the invention.

EXAMPLE 1

Run A—A 0.635 cm diameter by 12.2 m coiled, stainless steel tubular reactor 24 that was purged with nitrogen before use was used. The reactor was in a chamber and it was surrounded by dry insulation. Inlet lines 21 and 22 were provided for feeding isobutyraldehyde and catalyst solution, the lines being equipped with the necessary valves and controls to maintain pressure and to adjust feeding rates. The last 0.6 m of the tubular reactor 24 extended outside the insulated container and was wrapped with heating tape to allow heating the reaction product mixture prior to its entry into the distillation column 26. The exit 25 of the tubular reactor 24 was connected to a 40 tray Oldershaw distillation column 26 at tray 20. Isobutyraldehyde at an average feed rate of about 2 liters per hour and a 38 weight percent aqueous sodium hydroxide solution at an average feed rate of about 10 mL per hour were continuously fed through the tubular reactor at a temperature in the reactor of from about 90° C. to about 110° C. The catalyst was present at a concentration of approximately 0.6 mole percent sodium hydroxide based on isobutyraldehyde. The feed was continued for 37 hours with the average residence time of the reaction mixture in the tubular reactor 24 being about 6 minutes. A back pressure of from about 70 to 95 psig. was maintained in the system to minimize vaporization of the isobutyraldehyde during reaction. As the reaction product exited the tubular reactor it was heated in the tape-wrapped section 25 prior to directly entering the Oldershaw column 26 at tray 20. The column was fed at a rate of about two liters per hour and distillation was carried out at atmospheric pressure. In this specific example unreacted isobutyraldehyde and water were removed overhead via line 27 from column 26 and concentrated reaction product was removed from kettle 26A via line 29 at the base of the column. The distillation conditions and the composition of the reaction product crude recovered in kettle 26A at the bottom of the distillation column after the reaction had been stabilized were spot-analyzed and these results are set forth in Table I. The average residence time of material in kettle 26A was about 30 minutes. Six hours were required for stabilization of the system at the beginning of the reaction and distillation procedures and this period was not considered in the data presented in Table I.

Run B—A commercial scale reactor constructed essentially the same as the tubular reactor described in Run A was used to catalytically react isobutyraldehyde at a temperature of 123° C.±3° C. and a pressure of about 70 psig. Isobutyraldehyde was fed to the tubular reactor 24 at a liquid hourly space velocity of 0.1 hr.$^{-1}$; the catalyst was present at a concentration of approximately 0.6 mole percent based on isobutyraldehyde. The reaction was stabilized and then a fraction of the crude reaction product was removed from tubular reactor 24 at point 25 (suitably valved) and stored in a container. This crude had essentially the same composition as the crude product obtained using the tubular reactor described in Run A. The container was trans-shipped and subsequently the product was introduced into a 30 tray Oldershaw column 26 at tray 10; prior to entering the column it was preheated to about 137° C. The column was fed at a rate of 1.5 liters per hour and the distillation was carried out over a four hours period at a column pressure of 305 mm of mercury. Unreacted isobutyraldehyde and water were removed overhead from the column via line 27 and concentrated reaction product was removed from kettle 26A via line 29 at the base of the column. The distillation conditions and analysis of the composition of the reaction product recovered at the bottom of the distillation column are also set forth in Table I. The average residence time of material in kettle 26A was about 30 minutes. One hour was required for system stabilization. The results in Table I summarize the distillation conditions and show the unexpected results achieved by the process of this invention. One of the problems in the production of the 2,2,4trimethyl-1,3-pentanediol monoisobutyrates is the difficulty encountered in separating the isomeric mixture from by-products formed when the reaction product recovered from the reactor is not immediately subjected to an initial distillation. Particularly undesirable by products are the dimer and trimer of isobutyraldehyde, and the $C_{16}$ esters, namely, (i) 2,2,4-trimethyl-3-hydroxypent-1-yl 2,2,4trimethyl-3-hydroxypentanoate and (ii) 2,2,4-trimethyl-1-hydroxypent-3-yl 2,2,4trimethyl-3-hydroxypentanoate. Once formed, these species are difficult to remove from the desired 2,2,4-trimethyl-1,3-pentanediol monoisobutyrates, complicating the later refining steps and necessitating repeated distillations and decantations, as shown in the prior art previously referred to. However, as seen in the data in Table I, formation of these undesired species is unexpectedly and unpredictably minimized when the reaction product from tubular reactor 24 is immediately fed to the distillation column 26 and distilled. Thus, in Run A, which was performed in accord with this invention, the total of the average amounts of the sum of isobutyraldehyde dimer and trimer plus the $C_{16}$ esters in the concentrated reaction product recovered from the bottom of the distillation column was less than about 0.4 weight percent. However, in comparative Run B, which was performed in a manner consistent with prior conventional processes, the total amount of the sum of isobutyraldehyde dimer and trimer plus the $C_{16}$ esters in the concentrated reaction product recovered from the bottom of the distillation column was a significant amount, namely 5.9 weight percent; this is an amount about 15 times greater than the amount found in Run A. During the distillation the kettle temperature was maintained below 200° C. and the average residence time of the concentrate in the kettle was about 30 minutes.

TABLE I

| | Reaction Progress, Hours | | | | | | |
|---|---|---|---|---|---|---|---|
| | Run A | | | | | | Run B |
| Hours | 7-9 | 12-14 | 21-23 | 29-31 | 32-34 | 35-37 | 2-3 |
| Temp., °C. | | | | | | | |
| Preheat | 121 | 124 | 141 | 137 | 136 | 136 | 137 |
| Kettle | 183 | 187 | 187 | 183 | 186 | 190 | 183 |
| Overhead | 64 | 64 | 64 | 63 | 63 | 63 | 62 |
| Reflux Ratio$^{(a)}$ | 20:1 | 20:1 | 4:1 | 7:1 | 10:1 | 7:1 | 8:1 |
| Anal. of Conc., %$^{(b)}$ | | | | | | | |
| IBT | 86.5 | 85.8 | 86.1 | 88.6 | 87.7 | 87.5 | 88.2 |
| Dimer | 0.1 | 0.06 | 0.1 | 0.05 | 0.08 | 0.09 | 1.5 |
| Trimer | 0 | 0 | 0.03 | 0 | 0 | 0 | 2.3 |
| $C_{16}$ Esters | 0.2 | 0.2 | 0.3 | 0.3 | 0.2 | 0.2 | 2.1 |
| Diol | 2.3 | 2.2 | 2.1 | 2.1 | 2.4 | 2.3 | 1.0 |
| Diester | 1.9 | 1.6 | 1.3 | 1.0 | 1.6 | 1.6 | 0.3 |
| IBOH | 0.8 | 0.9 | 1.0 | 0.9 | 0.9 | 0.9 | 0.01 |
| IBAL | 4.6 | 4.9 | 4.5 | 4.0 | 4.4 | 5.5 | 3.3 |

$^{(a)}$Make:Return
$^{(b)}$Conc. is reaction mixture recovered from bottom of column.
IBT - 2,2,4-trimethyl-3-hydroxypentyl isobutyrate.
Dimer - 2,2,4-trimethyl-3-hyroxypentaldehyde.
Trimer - 2,6-diisopropyl-5,5-dimethyl-4-dioxanol.
$C_{16}$ Esters - isomers identified in Example 1.
Diol - 2,2,4-trimethyl-1,3-pentanediol.
Diester - 2,2,4-trimethyl-1,3-pentanediol diisobutyrate.
IBOH - isobutanol.
IBAL - isobutyraldehyde.

EXAMPLE 2

The effect residence time and temperature in the kettle at the base of initial distillation column 26 have on the stability of the isomers of 2,2,4-trimethyl-1,3-pentanediol monoisobutyrate is illustrated in this example. It was unexpectedly discovered that both factors caused decomposition of this product to unwanted diol and diester, which are formed in equimolar amounts, whose presence then complicate further refining and recovery because of difficulties in separating them from the desired product and, in addition, their formation represents a loss of the desired product.

In this example, isobutyraldehyde was condensed in a manner essentially the same as described in Example 1 and the unreacted isobutyraldehyde and water were removed at high vacuum (ca. 10 mm of Hg) and low temperature (ca. 60° C.). In this manner a crude was obtained that is representative of the crude product that would be recovered from kettle 26A. This material had a 2,2,4trimethyl-1,3-pentanediol monoisobutyrate content of 95 weight percent, 2.7 weight percent of diol, 0.3 weight percent of diester and 0.6 weight percent of isobutanol. The effect the residence time and temperature on diol and diester formation in distillation column kettle 26A was studied by heating samples of the material in sealed flasks at selected temperatures and time periods.

In each instance a 20 g sample was placed in the flask, purged with nitrogen and sealed. The flask was heated in an oil bath at the temperatures and for the times indicated in each of the following series.

In the first series, the temperature of the oil bath was 160° C. and four samples were heated for periods of 0.25 hour, one hour, two hours and four hours, respectively. The heated samples were analyzed for diester, 2,2,4-trimethyl-1,3-pentyl diisobutyrate, content as an indication of the extent of decomposition. This is Series A and corresponds to Curve A in FIG. 2.

A second set of four samples was evaluated as was done for Series A at an oil bath temperature of 170° C. and samples were then removed and analyzed for diester as was done for Series A. This is Series B and corresponds to Curve B in FIG. 2.

Another set of four samples was evaluated in the same manner at an oil bath temperature of 180° C. and samples were then removed and analyzed for diester as was done for Series A. This is Series C and corresponds to Curve C in FIG. 2.

Another set of four samples was evaluated in the same manner at an oil bath temperature of 190° C. and samples were then removed and analyzed for diester as was done for Series A. This is Series D and corresponds to Curve D in FIG. 2.

Another set of four samples was evaluated in the same manner at an oil bath temperature of 200° C. and samples were then removed and analyzed for diester as was done for Series A. This is Series E and corresponds to Curve E in FIG. 2.

Another set of four samples was evaluated in the same manner at an oil bath temperature of 220° C. and samples were then removed and analyzed for diester as was done for Series A. This is Series F and corresponds to Curve F in FIG. 2.

The amount of diester formed by decomposition of 2,2,4-trimethyl-1,3-pentanediol monoisobutyrate in each of the series is tabulated in Table II.

TABLE II

| Series | A | B | C | D | E | F |
|---|---|---|---|---|---|---|
| Temp., ° C. ± 3° C. | 160 | 170 | 180 | 190 | 200 | 220 |

TABLE II-continued

| Series | A | B | C | D | E | F |
|---|---|---|---|---|---|---|
| Wt. % Diester | | | | | | |
| initial | 0.35 | 0.35 | 0.35 | 0.35 | 0.35 | 0.35 |
| after 0.25 hours | 0.35 | 0.35 | 0.38 | 0.45 | 0.6 | 0.95 |
| after 1 hour | 0.4 | 0.45 | 0.5 | 0.6 | 0.8 | 2.3 |
| after 2 hours | 0.45 | 0.6 | 0.8 | 1 | 1.5 | 4 |
| after 4 hours | 0.65 | 0.8 | 1.2 | 1.7 | 2.4 | 7 |

The data shows the unexpected and unpredictables rapid rise in decomposition rate of the 2,2,4-trimethyl-1-hydroxypentyl isobutyrate at increased residence times and temperatures in kettle 26A in the presence of catalyst and the need to carefully regulate the process at this stage. This has not heretofore been reported. Thus, temperatures below about 200° C. and residence times up to about 0.5 hour in a continuous distillation are preferred.

EXAMPLE 3

Run A—Isobutyraldehyde was reacted to form the 2,2,4-trimethyl-1,3-pentanediol monoisobutyrates using the equipment used in Example 1 and following essentially the same reaction conditions. As the 2,2,4-trimethyl-1,3-pentanediol monoisobutyrates reaction product mixture exited reactor 24 it was heated in tape-wrapped section 25 to about 121° C. and directly introduced into a 40 tray Oldershaw distillation column 26 at tray 20 and distilled as described in Example 1. The distillation conditions and the composition of the reaction product crude recovered in kettle 26A at the bottom of the distillation column are set forth in Table III. The average residence time of material in kettle 26A was 15 minutes and the kettle temperature was kept at about 189° C.

Run B—For comparative purposes Run A was repeated. However, in this run the material entering the distillation column was preheated to 133° C. and the kettle temperature was kept at about 208° C.; residence time was also 15 minutes. Results are set forth in Table III; see footnotes to Table I for product definitions.

TABLE III

| | Run A | Run B |
|---|---|---|
| Hours | 2-3 | 2-4 |
| Temp., °C. | | |
| Preheat | 121 | 133 |
| Kettle | 189 | 208 |
| Overhead | 63 | 63 |
| Anal. of Conc. % | | |
| IBT | 89.3 | 89.4 |
| Diol | 1.7 | 2.3 |
| Diester | 0.8 | 1.8 |
| IBOH | 0.9 | 0.8 |
| IBAL | 4.2 | 3.2 |

The significantly higher amounts of diol and diester formed even at a short residence time of 15 minutes when the kettle temperature is 208° C. rather than 189° C. are evident. As shown in Examples 2 and 3 temperatures below 200° C. are preferred.

EXAMPLE 4

Using the equipment described in Example 1, Run B, and essentially the same conditions, isobutyraldehyde was catalytically reacted to produce the 2,2,4trimethyl-1,3-pentanediol monoisobutyrates. The reaction product exited reactor 24 and directly entered distillation column 26 at tray 20 at a rate of about 2 liters per hour. Unreacted dry isobutyraldehyde was recycled via lines 31 and 21 and water with a small amount of isobutyraldehyde were removed overhead via line 27 and separated in kettle 28. Crude concentrated reaction product collected in kettle 26A and was conveyed via line 29 to a storage vessel. The average residence time of crude concentrate in kettle 26A ranged from about 60 to about 120 minutes. A 2,699 g portion of the crude concentrate was washed twice, the first wash was carried out in vessel 30 using about 10 volume percent water based on concentrate and the second was was carried out in vessel 35 using about 4 volume percent water. The twice-washed crude concentrate was heated to 200° C. to 220° C. and introduced into the distillation column 39 via line 38. Distillation was carried out at a column 39 pressure of 100 torr and a kettle 39A temperature of about 195° C.±3° C. The desired purified 2,2,4 trimethyl-1,3-pentanediol monoisobutyrates mixture was taken as a side-make via line 40 above the feed point from column 39, where about a 1:1 reflux ratio was maintained; lights were removed as the head-make at a point above the side-make and the head was kept at nearly total reflux to minimize product loss overhead; a cold trap was used to collect material not recovered in the head-make; residues collected in kettle 39A and a kettle make was removed at a rate to maintain an average residence time in kettle 39A of less than one hour. The refined 2,2,4-trimethyl-3-hydroxypentyl isobutyrate side-make weighed 2,358 g and had a purity of 98.3%. Product decomposition to undesired diol and diester during distillation in column 39 was neglegible, less than 0.5 weight percent, (5.4 g of the diol and 4.8 g of the diester being formed) as a result of the short average residence time and low temperature in kettle 39A and low catalyst cation content in the feed to column 39. Table IV shows the compositions of the crude concentrate feed introduced into column 39 and of the various fractions recovered after the distillation had terminated; see footnotes to Table I for product definitions.

TABLE IV

| | IBT, % | Diol, % | Diester, % | IBOH, % | IBAL, % |
|---|---|---|---|---|---|
| Feed | 90.1 | 1.8 | 2.3 | 1.2 | 1.6 |
| Recovered Fractions | | | | | |
| Refined IBT | 98.3 | 0.87 | 0.63 | 0.04 | 0.04 |
| Head-make | 61.0 | 24.1 | 0 | 7.7 | 1.2 |
| Coldtrap | 4.5 | 1.7 | 0 | 33.5 | 49.5 |
| Kettle-make | 60.7 | 0 | 34.3 | 0 | 0.3 |
| Kettle residue | 66.0 | 0.13 | 33.0 | 0 | 0.3 |

EXAMPLE 5

A 1,790 grams portion of crude concentrate prepared in Example 4 was purified by following essentially the same procedure described in Example 4. In this instance, however, the pressure in distillation column 39 was 250 torr and kettle 39A temperature was about 215° C.±3° C. The refined 2,2,4-trimethyl-1,3-pentanediol monoisobutyrates had a purity of 98.1% and weighed 1,530 g. Negligible decomposition, less than 0.1 weight percent (0.1 g of the diol and 1.2 g of the diester being formed) resulted, for the reasons set forth in Example 4. Table V shows the analysis of the fractions recovered after the distillation had terminated; see footnotes to Table I for product definitions.

TABLE V

| Recovered Fractions | IBT, % | Diol, % | Diester, % | IBOH, % | IBAL, % |
|---|---|---|---|---|---|
| Refined IBT | 98.1 | 1.2 | 0.37 | 0.05 | 0.04 |
| Head-make | 31.2 | 22.2 | 0 | 21.7 | 5.5 |
| Coldtrap | 1.4 | 0.61 | 0 | 23.1 | 63.7 |
| Kettle-make | 68.2 | 0 | 31.4 | 0 | 0.1 |
| Kettle residue | 66.4 | 0.15 | 32.3 | 0 | 0.1 |

EXAMPLE 6

For comparative purposes a 2,468 grams portion of crude concentrate prepared in Example 4 was purified by the procedure described in Example 4 with the exception that the crude was subjected to only a single water wash using 10 volume percent water as the wash medium to examine the effect of higher levels of catalyst present in the system on product decomposition during final distillation. The single water wash of crude material still permitted recovery of high quality 2,2,4-trimethyl-1,3-pentanediol monoisobutyrates, but about six percent of the product originally present in the feed decomposed to diol and diester (48.7 g of the diol and 77.9 g of the diester being formed) even under the mild distillation conditions employed. This is significantly more than was observed in Examples 4 and 5. In this distillation the pressure in distillation column 9 was 100 torr and kettle 39A temperature was about 195° C.±3° C. The refined 2,2,4-trimethyl-1,3-pentanediol monoisobutyrates had a purity of 97% and weighed 1,820 g. Table VI shows the analysis of the fractions recovered after distillation had terminated; see footnotes to Table I for product identification.

TABLE VI

| Recovered Fractions | IBT, % | Diol, % | Diester, % | IBOH, % | IBAL, % |
|---|---|---|---|---|---|
| Refined IBT | 97.0 | 2.0 | 0.71 | 0.03 | 0.04 |
| Head-make | 30.4 | 48.5 | 0 | 10.4 | 1.8 |
| Cold-trap | 4.3 | 7.6 | 0 | 29.5 | 45.9 |
| Kettle-make | 61.1 | 0.92 | 29.7 | 0 | 0.2 |
| Kettle residue | 70.0 | 1.0 | 28.7 | 0 | 0.1 |

What is claimed is:

1. In a process for producing and recovering a trisubstituted glycol monoester of the formula:

(1)

wherein X is a hydrogen atom or a group with the proviso that at any one time only one X group is a hydrogen atom and R' and R" individually are hydrocarbyl groups containing from 1 to about 10 carbon atoms, by the condensation at elevated temperature of a $C_4$ to $C_{12}$ aldehyde in contact with a strong base catalyst and recovering the trisubstituted glycol monoester produced, the improvement in the recovering step comprising flowing the reaction product mixture directly and immediately to an initial distillation of the reaction product mixture before said mixture essentially cools or comes into contact with added aqueous medium, whereby untreated aldehyde and any water present are removed overhead and crude concentrated reaction product mixture bottoms comprising trisubstituted glycol monoester are recovered as a bottoms stream and said concentrated crude bottoms stream is subsequently further refined.

2. The process of claim 1 wherein the temperature of said bottoms is from about 150° C. to about 210° C. and the residence time of said bottoms before recovery as a bottoms stream does not exceed 120 minutes.

3. The process of claim 1 wherein the temperature of said bottoms is from about 160° C. to about 200° C. and the residence time of said bottoms before recovery as a bottoms stream does not exceed 60 minutes.

4. The process of claim 1 wherein the temperature of said bottoms is from about 160° C. to about 200° C. and the residence time of said bottoms before recovery as a bottoms stream does not exceed 30 minutes.

5. The process of claim 1 wherein the temperature of said bottoms is from about 180° C. to about 190° C. and the residence time of said bottoms before recovery as a bottoms stream does not exceed 60 minutes.

6. The process of claim 1 wherein the temperature of said bottoms is from about 180° C. to about 190° C. and the residence time of said bottoms before recovery as a bottoms stream does not exceed 30 minutes.

7. The process of claim 1 wherein said aldehyde is isobutyraldehyde, said catalyst is an aqueous sodium hydroxide solution containing from about 30 weight percent to about 60 weight percent sodium hydroxide and wherein said trisubstituted glycol monoester is 2,2,4-trimethyl-1,3-pentanediol monoisobutyrate.

8. The process of claim 7 wherein said aqueous sodium hydroxide solution contains from about 35 weight percent to about 60 weight percent sodium hydroxide.

9. The process of claim 2 wherein said aldehyde is isobutyraldehyde, said catalyst is an aqueous sodium hydroxide solution containing from about 35 weight percent to about 60 weight percent sodium hydroxide and wherein said trisubstituted glycol monoester is 2,2,4-trimethyl -1,3-pentanediol monoisobutyrate.

10. The process of claim 3 wherein said aldehyde is isobutyraldehyde, said catalyst is an aqueous sodium hydroxide solution containing from about 35 weight percent to about 60 weight percent sodium hydroxide and wherein said trisubstituted glycol monoester is 2,2,4-trimethyl-1,3-pentanediol monoisobutyrate.

11. The process of claim 4 wherein said aldehyde is isobutyraldehyde, said catalyst is an aqueous sodium hydroxide solution containing from about 35 weight percent to about 60 weight percent sodium hydroxide and wherein said trisubstituted glycol monoester is 2,2,4-trimethyl-1,3-pentanediol monoisobutyrate.

12. The process of claim 5 wherein said aldehyde is isobutyraldehyde, said catalyst is an aqueous sodium hydroxide solution containing from about 35 weight percent to about 60 weight percent sodium hydroxide and wherein said trisubstituted glycol monoester is 2,2,4trimethyl-1,3-pentanediol monoisobutyrate.

13. The process of claim 6 wherein said aldehyde is isobutyraldehyde, said catalyst is an aqueous sodium hydroxide solution containing from about 35 weight percent to about 60 weight percent sodium hydroxide and wherein said trisubstituted glycol monoester is 2,2,4trimethyl-1,3-pentanediol monoisobutyrate.

14. The process of claim 1 wherein said concentrated crude bottoms stream is refined by a series of water washes and separations and the water washed crude is distilled to recover refined trisubstituted glycol monoester of Formula I.

15. The process of claim 2 wherein said concentrated crude bottoms stream is refined by a series of water washes and separations and the water washed crude is distilled to recover refined trisubstituted glycol monoester of Formula I.

16. The process of claim 3 wherein said concentrated crude bottoms stream is refined by a series of water washes and separations and the water washed crude is distilled to recover refined trisubstituted glycol monoesters of Formula I.

17. The process of claim 4 wherein said concentrated crude bottoms stream is refined by a series of water washes and separations and the water washed crude is distilled to recover refined trisubstituted glycol monoesters of Formula I.

18. The process of claim 5 wherein said concentrated crude bottoms stream is refined by a series of water washes and separations and the water washed crude is distilled to recover refined trisubstituted glycol monoesters of Formula I.

19. The process of claim 6 wherein said concentrated crude bottoms stream is refined by a series of water washes and separations and the water washed crude is distilled to recover refined trisubstituted glycol monoesters of Formula I.

20. The process of claim 7 wherein said concentrated crude bottoms stream is refined by a series of water washes and separations and the water washed crude is distilled to recover refined 2,2,4-trimethyl-1,3-pentanediol monoisobutyrate.

21. The process of claim 8 wherein said concentrated crude bottoms stream is refined by a series of water washes and separations and the water washed crude is distilled to recover refined 2,2,4-trimethyl 1,3-pentanediol monoisobutyrate.

22. The process of claim 9 wherein said concentrated crude bottoms stream is refined by a series of water washes and separations and the water washed crude is distilled to recover refined 2,2,4-trimethyl-1,3-pentanediol monoisobutyrate.

23. The process of claim 10 wherein said concentrated crude bottoms stream is refined by a series of water washes and separations and the water washed crude is distilled to recover refined 2,2,4-trimethyl-1,3-pentanediol monoisobutyrate.

24. The process of claim 11 wherein said concentrated crude bottoms stream is refined by a series of water washes and separations and the water washed crude is distilled to recover refined 2,2,4-trimethyl-1,3-pentanediol monoisobutyrate.

25. The process of claim 12 wherein said concentrated crude bottoms stream is refined by a series of water washes and separations and the water washed crude is distilled to recover refined 2,2,4-trimethyl-1,3-pentanediol monoisobutyrate.

26. The process of claim 13 wherein said concentrated crude bottoms stream is refined by a series of water washes and separations and the water washed crude is distilled to recover refined 2,2,4-trimethyl-1,3-pentanediol monoisobutyrate.

* * * * *

UNITED STATES PATENT AND TRADEMARK OFFICE
CERTIFICATE OF CORRECTION

PATENT NO. : 4,883,906
DATED : November 28, 1989
INVENTOR(S) : J. N. Argyropoulos, et al.

It is certified that error appears in the above-identified patent and that said Letters Patent is hereby corrected as shown below:

Column 3, line 1, formula

""

should read

----

Signed and Sealed this

Sixteenth Day of July, 1991

*Attest:*

HARRY F. MANBECK, JR.

*Attesting Officer*    Commissioner of Patents and Trademarks